(12) United States Patent
Kimura et al.

(10) Patent No.: US 12,280,335 B2
(45) Date of Patent: Apr. 22, 2025

(54) PURIFICATION SYSTEM, PURIFICATION METHOD, MEMBRANE SEPARATION DEVICE, AND SOLVENT MANUFACTURING METHOD

(71) Applicant: NITTO DENKO CORPORATION, Ibaraki (JP)

(72) Inventors: Naomichi Kimura, Ibaraki (JP); Yuri Ito, Ibaraki (JP); Tomoya Hirai, Ibaraki (JP); Shinya Nishiyama, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 320 days.

(21) Appl. No.: 17/641,988

(22) PCT Filed: Sep. 16, 2020

(86) PCT No.: PCT/JP2020/035108
§ 371 (c)(1),
(2) Date: Mar. 10, 2022

(87) PCT Pub. No.: WO2021/054368
PCT Pub. Date: Mar. 25, 2021

(65) Prior Publication Data
US 2022/0401884 A1      Dec. 22, 2022

(30) Foreign Application Priority Data

Sep. 18, 2019    (JP) .................................. 2019-169217

(51) Int. Cl.
*B01D 61/02*    (2006.01)
*B01D 61/08*    (2006.01)
(Continued)

(52) U.S. Cl.
CPC ........... *B01D 61/58* (2013.01); *B01D 61/025* (2013.01); *B01D 61/08* (2013.01); *B01D 61/362* (2013.01);
(Continued)

(58) Field of Classification Search
CPC ................ B01D 61/025; B01D 61/362; B01D 2311/06; B01D 2313/125; C12H 1/063; C12G 3/08
See application file for complete search history.

(56) References Cited

U.S. PATENT DOCUMENTS

| 4,925,562 A | 5/1990 | te Hennepe et al. |
| 4,944,882 A | 7/1990 | Ray et al. |

(Continued)

FOREIGN PATENT DOCUMENTS

| EP | 1611940 A1 * | 1/2006 | ........... B01D 61/142 |
| JP | S63-116705 A | 5/1988 | |

(Continued)

OTHER PUBLICATIONS

Moeller-Hergt—EP1611940A1 machine translation—Jul. 24, 2004 (Year: 2004).*

(Continued)

*Primary Examiner* — Bradley R Spies
(74) *Attorney, Agent, or Firm* — HAUPTMAN HAM, LLP

(57) ABSTRACT

A purification system is for purifying a mixture containing a first solvent, a second solvent, and an impurity. The purification system includes a first membrane separation device including a pervaporation membrane and a second membrane separation device including a filtration membrane. The pervaporation membrane separates the mixture into a first permeated fluid and a first concentrated fluid. The first permeated fluid has a lower concentration of the impurity than that in the mixture, and the first concentrated fluid (Continued)

has a higher concentration of the impurity than that in the mixture. The filtration membrane separates the first concentrated fluid into a second permeated fluid and a second concentrated fluid. The second permeated fluid has a lower concentration of the impurity than that in the first concentrated fluid, and the second concentrated fluid has a higher concentration of the impurity than that in the first concentrated fluid.

20 Claims, 6 Drawing Sheets

(51) Int. Cl.
    *B01D 61/36* (2006.01)
    *B01D 61/58* (2006.01)
    *B01D 71/02* (2006.01)
    *B01D 71/70* (2006.01)
    B01D 69/14 (2006.01)

(52) U.S. Cl.
    CPC ....... *B01D 61/366* (2013.01); *B01D 71/0281* (2022.08); *B01D 71/70* (2013.01); *B01D 69/147* (2013.01); *B01D 2311/08* (2013.01); *B01D 2311/2512* (2022.08); *B01D 2311/2523* (2022.08); *B01D 2317/022* (2013.01); *B01D 2317/08* (2013.01)

(56) References Cited

U.S. PATENT DOCUMENTS

| 2014/0163264 | A1 | 6/2014 | Takahashi et al. |
| 2016/0326473 | A1* | 11/2016 | Thurnheer ........... B01D 61/027 |

FOREIGN PATENT DOCUMENTS

| JP | H2-293023 A | 12/1990 |
| JP | H6-69175 A | 3/1994 |
| JP | H8-252434 A | 10/1996 |
| JP | H11-16873 A | 1/1999 |
| JP | 2012-81463 A | 4/2012 |
| JP | 2013-23439 A | 2/2013 |
| JP | 5819987 B2 | 11/2015 |
| WO | 2016/057764 A1 | 4/2016 |

OTHER PUBLICATIONS

The Extended European Search Report issued on Sep. 1, 2023 for corresponding European Patent Application No. 20866606.5 (18 pages).
Vane et al., "Hydrophobic zeolite-silicone rubber mixed matrix membranes for ethanol-water separation: Effect of zeolite and silicone component selection on pervaporation performance", Journal of Membrane Science, vol. 308, No. 1-2, 2008, pp. 230-241 (12 pages).
Ray et al., "Synergistic, membrane-based hybrid separation systems", Journal of Membrane Science, vol. 62, No. 3, Oct. 30, 1991, pp. 347-369 (23 pages).
Cen et al., "Non-porous membranes and their application", Chemie-Ingenieur-Technik, Weinheim, Germany, vol. 65, No. 8, Aug. 1, 1993, pp. 901-913, along with an English machine translation (26 pages).
International Search Report issued for corresponding International Patent Application No. PCT/JP2020/035108 on Nov. 10, 2020, along with an English Translation.
Written Opinion issued for corresponding International Patent Application No. PCT/JP2020/035108 on Nov. 10, 2020, along with an English Translation.
Communication pursuant to Article 94(3) EPC issued on May 27, 2024 for corresponding European Patent Application No. 20 866 606.5 (10 pages).
Office Action issued on Sep. 3, 2024 for corresponding Japanese Patent Application No. 2020-155608, along with an English machine translation (8 pages).
Office Action issued on Apr. 23, 2024 for corresponding Chinese Patent Application No. 202080057849.6, along with an English machine translation (12 pages).
Communication pursuant to Article 94(3) EPC issued on Dec. 4, 2024 for corresponding European Patent Application No. 20 866 606.5 (9 pages).

\* cited by examiner

PURIFICATION SYSTEM, PURIFICATION METHOD, MEMBRANE SEPARATION DEVICE, AND SOLVENT MANUFACTURING METHOD

CROSS REFERENCE TO RELATED APPLICATION

This application is a National Stage of International Application No. PCT/JP2020/035108, filed on Sep. 16, 2020, which designates the United States and was published in Japan, and which is based upon and claims priority to Japanese Patent Application No. 2019-169217 filed on Sep. 18, 2019 in the Japan Patent Office. All of the aforementioned applications are hereby incorporated by reference in their entireties.

TECHNICAL FIELD

The present invention relates to a purification system, purification method, and membrane separation device suitable for purifying a mixture containing a plurality of solvents and an impurity, such as an aqueous solution containing a lower alcohol and an impurity other than the lower alcohol, and a solvent manufacturing method including a method for purifying the mixture.

BACKGROUND ART

Mixtures containing a plurality of solvents are used as washing solutions, for example, in the process of manufacturing separation membranes (e.g., reverse osmosis membranes (RO membranes)), semiconductors, and the like. For example, Patent Literature 1 discloses, as a washing solution for semiconductor wafers, a mixture containing isopropyl alcohol and pure water. Washing solutions are desirably used repeatedly in view of reducing an environmental burden. However, repeating use of washing solutions increases the concentration of an impurity derived from a washing target in the washing solutions, resulting in an insufficient washing effect. Therefore, when washing solutions are used repeatedly, it is necessary to maintain a low impurity concentration in the washing solutions.

The concentration of an impurity can be adjusted, for example, by purifying a washing solution to remove the impurity from the washing solution. A common method for purifying a washing solution is a distillation method. A conceivable purification method other than the distillation method is a method (absorption method) in which a washing solution is brought into contact with an absorbing material such as activated carbon to remove an impurity.

CITATION LIST

Patent Literature

Patent Literature 1: JP 5819987 B2
Patent Literature 2: JP H8(1996)-252434 A

SUMMARY OF INVENTION

Technical Problem

However, the distillation method requires provision of a large amount of energy to a mixture to be purified. In the absorption method, a lot of absorbing materials need to be used to sufficiently remove an impurity from a mixture to be purified. In the absorption method, it is also necessary that an absorbing material having absorbed an impurity be subjected to recycling. As just described, both the distillation and absorption methods are not efficient enough.

Therefore, the present invention aims to provide a purification system capable of efficiently purifying a mixture containing a plurality of solvents.

Solution to Problem

As a result of intensive studies, the present inventors have found that an impurity in a mixture containing a plurality of solvents can be removed by, unexpectedly, a pervaporation method. The pervaporation method is commonly used as a method for increasing the concentration of a lower alcohol in a mixture liquid containing water and the lower alcohol (for example, in Patent Literatures 1 and 2). However, as far as the present inventors know, use of the pervaporation method for purification of a mixture containing a plurality of solvents has not been reported. The present inventors made further studies on the basis of the new finding on the pervaporation method and have completed the present invention.

The present invention provides a purification system for purifying a mixture containing a first solvent, a second solvent, and an impurity other than the first solvent and the second solvent, the purification system including:
  a first membrane separation device including a pervaporation membrane that separates the mixture into a first permeated fluid and a first concentrated fluid, the first permeated fluid having a lower concentration of the impurity than that in the mixture and having a higher concentration of the first solvent than that in the mixture, the first concentrated fluid having a higher concentration of the impurity than that in the mixture and having a lower concentration of the first solvent than that in the mixture; and
  a second membrane separation device including a filtration membrane that separates the first concentrated fluid into a second permeated fluid and a second concentrated fluid, the second permeated fluid having a lower concentration of the impurity than that in the first concentrated fluid, the second concentrated fluid having a higher concentration of the impurity than that in the first concentrated fluid.

The present invention also provides a method for purifying a mixture containing a first solvent, a second solvent, and an impurity other than the first solvent and the second solvent, the purification method including a first separation step of decreasing, in a state where the mixture is in contact with one surface of the pervaporation membrane, a pressure in a space adjacent to the other surface of the pervaporation membrane to obtain a first permeated fluid on the other surface side and a first concentrated fluid on the one surface side, the first permeated fluid being to be reused, having a lower concentration of the impurity than that in the mixture, and having a higher concentration of the first solvent than that in the mixture, the first concentrated fluid having a higher concentration of the impurity than that in the mixture and having a lower concentration of the first solvent than that in the mixture.

The present invention also provides a membrane separation device including a pervaporation membrane that separates a mixture containing a first solvent, a second solvent, and an impurity other than the first solvent and the second solvent into a permeated fluid and a concentrated fluid, the permeated fluid being to be reused, having a lower concentration of the impurity than that in the mixture, and having a higher concentration of the first solvent than that in the mixture, the concentrated fluid having a higher concentration of the impurity than that in the mixture and having a lower concentration of the first solvent than that in the mixture.

Advantageous Effects of Invention

The present invention can provide a purification system capable of efficiently purifying a mixture containing a plurality of solvents.

DESCRIPTION OF EMBODIMENTS

Figure 1:
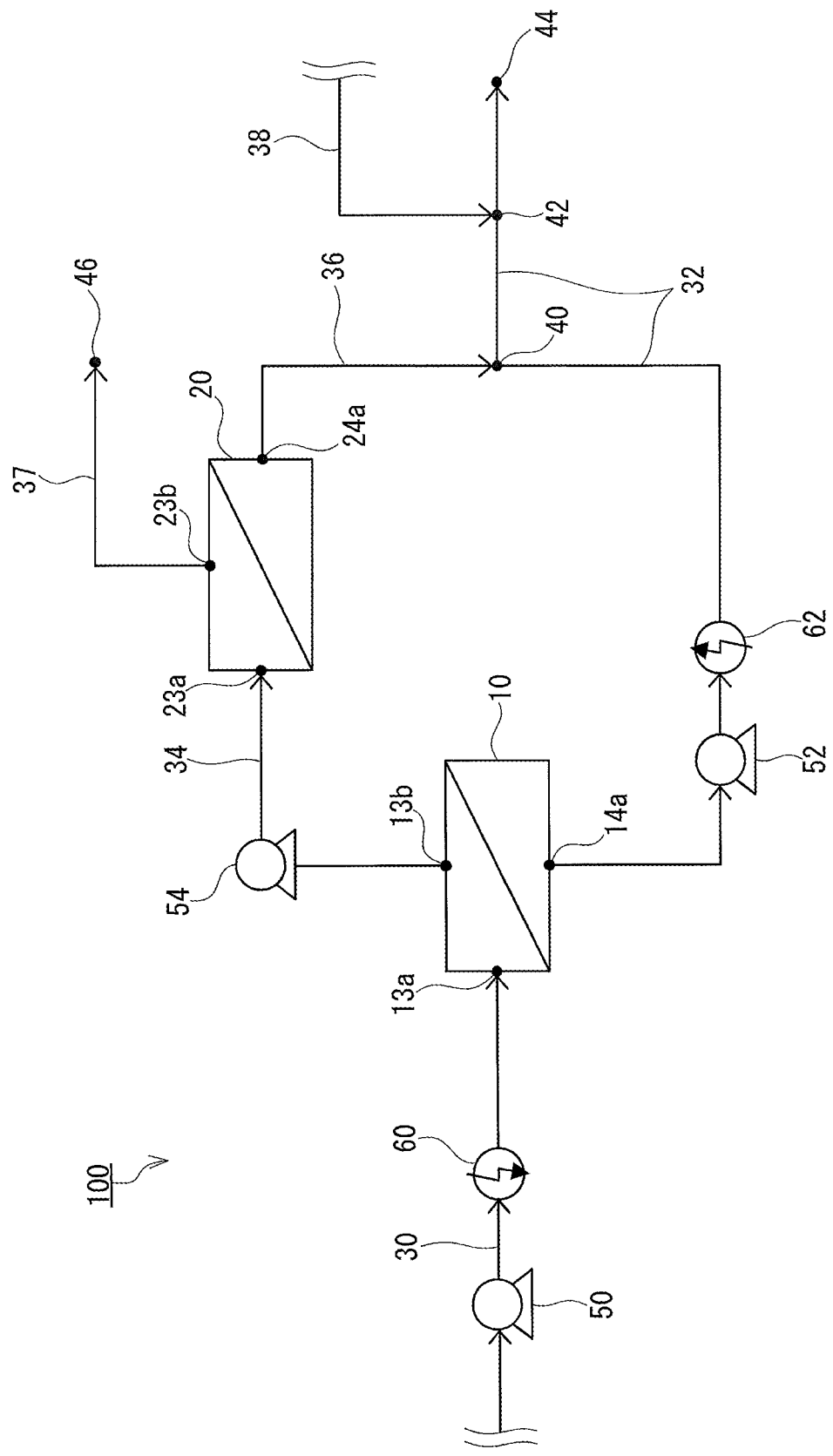
FIG. 1 is a configuration diagram showing a purification system according to one embodiment of the present invention.

Hereinafter, the present invention will be described in detail. The following description is not intended to limit the present invention to a specific embodiment.
<Purification System>
As shown in FIG. 1, a purification system 100 of the present embodiment includes a first membrane separation device 10 and a second membrane separation device 20. The first membrane separation device 10 is a membrane separation device for performing membrane separation using a pervaporation membrane (PV membrane) for a mixture to be purified. The pervaporation membrane of the first membrane separation device 10 can separate the mixture to be purified into a first permeated fluid and a first concentrated fluid. The first permeated fluid is reused, for example, for a given application (e.g., as a washing solution). The second membrane separation device 20 is a membrane separation device for performing membrane separation using a filtration membrane for the first concentrated fluid discharged from the first membrane separation device 10. The filtration membrane of the second membrane separation device 20 can separate the first concentrated fluid into a second permeated fluid and a second concentrated fluid. As described later, the second permeated fluid is, for example, mixed with the first permeated fluid and reused for a given application along with the first permeated fluid. Herein, "first concentrated fluid" and "second concentrated fluid" are sometimes referred to as "first non-permeated fluid" and "second non-permeated fluid", respectively.

In the present embodiment, the mixture to be purified contains a first solvent, a second solvent, and an impurity other than the first solvent and the second solvent. The first solvent is typically a lower alcohol. The second solvent is typically water. One example of the mixture to be purified is a washing solution having been used in the process of manufacturing separation membranes (e.g., RO membranes) to wash a washing target such as a separation membrane. When the mixture is a washing solution having been used to wash a washing target, the impurity in the mixture is, for example, derived from the washing target. However, the mixture to be purified is not particularly limited as long as the mixture to be purified includes the plurality of solvents and the impurity. The mixture to be purified may be, for example, a waste solution resulting from one of various chemical processes. Herein, the mixture to be purified is sometimes simply referred to as "mixture".

The pervaporation membrane of the first membrane separation device 10 is a separation membrane capable of allowing the first solvent contained in the mixture to preferentially permeate therethrough by a pervaporation method. Therefore, the first permeated fluid separated by the pervaporation membrane has a lower concentration of the impurity than that in the mixture and has a higher concentration of the first solvent than that in the mixture. On the other hand, the first concentrated fluid has a higher concentration of the impurity than that in the mixture and has a lower concentration of the first solvent than that in the mixture.

The filtration membrane of the second membrane separation device 20 is a separation membrane capable of allowing the second solvent contained in the first concentrated fluid to preferentially permeate therethrough. Accordingly, the second permeated fluid separated by the filtration membrane has a lower concentration of the impurity than that in the first concentrated fluid. On the other hand, the second concentrated fluid has a higher concentration of the impurity than that in the first concentrated fluid.

The purification system 100 further includes a mixture supply passage 30. The mixture supply passage 30 is a passage connected to a mixture inlet (an inlet 13a) of the first membrane separation device 10 and configured to supply the mixture to the first membrane separation device 10 from, for example, a tank (not shown) storing the mixture. The mixture supply passage 30 is provided, for example, with a pump 50 and a heat exchanger 60. The heat exchanger 60 is located, for example, between the pump 50 and the first membrane separation device 10. The pump 50 is a pump for increasing the pressure on the mixture, and the flow rate of the mixture can be adjusted by controlling the pump 50. The heat exchanger 60 is, for example, a liquid-liquid heat exchanger that causes heat exchange between a heat medium such as hot water and the mixture, and is typically a plate heat exchanger.

The purification system 100 further includes a first discharge passage 32, a concentrated fluid supply passage 34, a second discharge passage 36, and a third discharge passage 37. The first discharge passage 32 is a passage connected to a permeated fluid outlet (an outlet 14a) of the first membrane separation device 10 and configured to discharge the first permeated fluid from the first membrane separation device 10. An opening (a discharge outlet 44) for discharging the first permeated fluid from the first discharge passage 32 is arranged in the first discharge passage 32. The first discharge passage 32 is provided, for example, with a pump 52 and a heat exchanger 62. The heat exchanger 62 is located between the pump 52 and the discharge outlet 44. The pump 52 is a pump for decreasing the pressure on the first membrane separation device 10, and the flow rate of the first permeated fluid can be adjusted by controlling the pump 52. The heat exchanger 62 is, for example, a gas-liquid or liquid-liquid heat exchanger that causes heat exchange between a cooling medium such as an antifreeze and the first permeated fluid, and is typically a plate heat exchanger.

The concentrated fluid supply passage 34 is a passage connecting a concentrated fluid outlet (an outlet 13b) of the first membrane separation device 10 and a concentrated fluid inlet (an inlet 23a) of the second membrane separation device 20 and configured to supply the first concentrated fluid to the second membrane separation device 20 from the first membrane separation device 10. The concentrated fluid supply passage 34 is provided, for example, with a pump 54. The pump 54 is a pump for increasing the pressure on the first concentrated fluid.

The second discharge passage 36 is a passage connected to a permeated fluid outlet (an outlet 24a) of the second membrane separation device 20 and configured to discharge the second permeated fluid from the second membrane separation device 20. The second discharge passage 36 joins, for example, the first discharge passage 32 at a joining point 40. The joining point 40 is located, for example, between the heat exchanger 62 and the discharge outlet 44. Since the second discharge passage 36 joins the first discharge passage 32, the first permeated fluid and the second permeated fluid can be mixed in the first discharge passage 32. The first discharge passage 32 may further be provided with a tank, and the second discharge passage 36 may be connected to the tank. In this case, the tank provided to the first discharge passage 32 can be regarded as the joining point 40.

The third discharge passage 37 is connected to a concentrated fluid outlet (an outlet 23b) of the second membrane separation device 20 and configured to discharge the second concentrated fluid from the second membrane separation device 20. An opening (a discharge outlet 46) for discharging the second concentrated fluid from the third discharge passage 37 is arranged in the third discharge passage 37.

The purification system 100 may further include a raw material supply passage 38. The raw material supply passage 38 is a passage connected to the first discharge passage 32 or the second discharge passage 36 and configured to supply a raw material containing at least one selected from the group consisting of the first solvent and the second solvent to the first discharge passage 32 connected to the raw material supply passage 38 or the second discharge passage 36 connected to the raw material supply passage 38. The raw material supply passage 38 is preferably connected to the first discharge passage 32 at the joining point 40 or a point 42 located downstream of the joining point 40. The point 42 located downstream of the joining point 40 is located, specifically, between the joining point 40 and the discharge outlet 44. In an example, the raw material supply passage 38 is connected to, for example, a tank (not shown) storing the raw material. It is preferable that the raw material be composed of at least one selected from the group consisting of the first solvent and the second solvent and substantially free of the impurity. The raw material supply passage 38 is suitable for adjusting the concentrations of the first solvent and the second solvent in a fluid mixture of the first permeated fluid and the second permeated fluid.

The purification system 100 may further include a third membrane separation device (not shown) for performing membrane separation using a pervaporation membrane for the first permeated fluid discharged from the first membrane separation device 10. The third membrane separation device is placed, for example, downstream of the heat exchanger 62 provided to the first discharge passage 32, particularly, between the heat exchanger 62 and the joining point 40. The pervaporation membrane included in the third membrane separation device may be the same as the pervaporation membrane included in the first membrane separation device 10 except for the membrane area, or may be different from the pervaporation membrane included in the first membrane separation device 10. The pervaporation membrane of the third membrane separation device allows the first solvent contained in the first permeated fluid to preferentially permeate therethrough by the pervaporation method. Using the third membrane separation device, a third permeated fluid having a much lower concentration of the impurity than that in the first permeated fluid and a much higher concentration of the first solvent than that in the first permeated fluid can be obtained. The third permeated fluid may be delivered to the joining point 40 and mixed with the second permeated fluid.

Each passage of the purification system 100 is formed of, for example, a metal or resin pipe.

As described above, the first solvent is typically a lower alcohol in the present embodiment. The lower alcohol is, for example, an alcohol having 5 or less carbon atoms. The lower alcohol may be a monohydric alcohol or a polyhydric alcohol. The lower alcohol may be linear or branched. Examples of the lower alcohol include methanol, ethanol, n-propanol, isopropanol (IPA), n-butanol, 2-butanol, isobutanol, t-butanol, and n-pentanol, and the lower alcohol is preferably IPA. The concentration of the first solvent in the mixture is, for example, 50 wt % or less, preferably 30 wt % or less, and more preferably 10 wt % or less. The lower limit of the concentration of the first solvent is, for example, but not particularly limited to, 1 wt %. Herein, the term "concentration" means a weight percent concentration determined when a mixture or fluid containing a target component has a temperature of 20° C., unless otherwise specified.

The second solvent is typically water in the present embodiment. The concentration of the second solvent in the mixture is, for example, more than 50 wt %, preferably 80 wt % or more, and more preferably 90 wt % or more. The upper limit of the concentration of the second solvent is, for example, but not particularly limited to, 99 wt %.

The impurity contained in the mixture to be purified is not particularly limited, and includes, for example, an organic compound and is preferably composed of an organic compound. However, the impurity may include an inorganic compound. The impurity may or may not be dissolved in the mixture. The boiling point of the organic compound included in the impurity is preferably higher than the boiling point of the first solvent contained in the mixture, and is, for example, 85° C. or higher. The organic compound may be a low-molecular compound having a molecular weight of 1000 or less. The organic compound includes, for example, at least one atom selected from the group consisting of a nitrogen atom and a sulfur atom, and typically includes at least one functional group selected from the group consisting of an amino group, an amide group, and a sulfonic acid group. In one example, in the process of manufacturing an RO membrane, a washing solution having been used to wash the RO membrane includes, in some cases, triethylamine (TEA), sodium lauryl sulfate (SLS), N,N-dimethylformamide (DMF), camphorsulfonic acid (CSA), p-toluenesulfonic acid (p-TSA), triethanolamine (TEtA), m-phenylenediamine (MPD), etc. as the impurity. The concentration of the impurity in the mixture is, for example, 300 ppm or more and may be 500 ppm or more. Herein, the term "ppm" means the mass percentage. The upper limit of the concentration of the impurity is, for example, but not particularly limited to, 1 wt %.

[First Membrane Separation Device]

Figure 2:
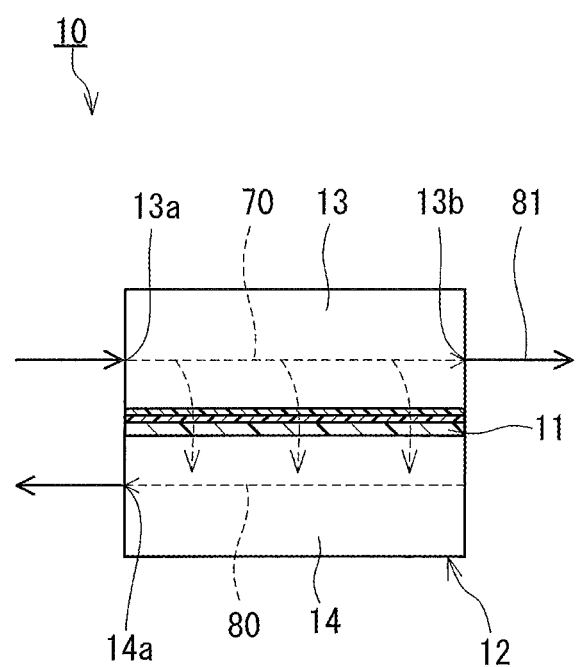
FIG. 2 is a schematic cross-sectional view showing an exemplary first membrane separation device.

As shown in FIG. 2, the first membrane separation device 10 includes a pervaporation membrane 11 and a tank 12. The tank 12 has a first chamber 13 and a second chamber 14. The pervaporation membrane 11 is placed in the tank 12. In the tank 12, the pervaporation membrane 11 separates the first chamber 13 and the second chamber 14 from each other. The pervaporation membrane 11 extends from one of a pair of wall surfaces of the tank 12 to the other.

The first chamber 13 has the inlet 13a and the outlet 13b. The second chamber 14 has the outlet 14a. The inlet 13a of the first chamber 13 is an opening for supplying a mixture 70 to the first membrane separation device 10. The outlet 14a of the second chamber 14 is an opening for discharging a first permeated fluid 80 obtained by allowing the mixture 70 to permeate through the pervaporation membrane 11 from the first membrane separation device 10. The outlet 13b of the first chamber 13 is an opening for discharging the mixture 70 (a first concentrated fluid 81) not having permeated through the pervaporation membrane 11 from the first membrane separation device 10. The inlet 13a, the outlet 13b, and the outlet 14a are arranged, for example, in wall surfaces of the tank 12.

Figure 3:
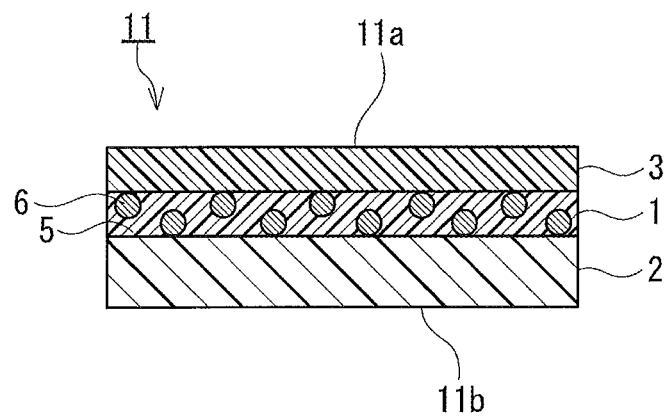
FIG. 3 is a cross-sectional view showing an exemplary pervaporation membrane.

The pervaporation membrane 11 is not particularly limited as long as the pervaporation membrane 11 can allow the first solvent contained in the mixture 70 to preferentially permeate therethrough. As shown in FIG. 3, the pervaporation membrane 11 includes, for example, a separation functional layer 1. The pervaporation membrane 11 may further include a porous support 2 supporting the separation functional layer 1 and a protective layer 3 protecting the separation functional layer 1. The separation functional layer 1 is located, for example, between the porous support 2 and the protective layer 3.

The separation functional layer 1 includes, for example, a matrix 5 and filler(s) 6. The fillers 6 are dispersed in the matrix 5 and embedded in the matrix 5. In the embodiment shown in FIG. 3, the fillers 6 are separated from each other. However, the fillers 6 may partially aggregate.

The material of the matrix 5 is not particularly limited, and examples thereof include a silicone resin and a polyolefin resin such as polypropylene. The matrix 5 including a silicone resin allows a lower alcohol to preferentially permeate therethrough and is suitable for reducing permeation of an organic compound other than lower alcohols, for example, an organic compound including an amino group, an amide group, and a sulfonic acid group.

The filler 6 includes, for example, an inorganic material such as a zeolite. The zeolite included in the filler 6 is preferably a high-silica zeolite having a high ratio of silica to alumina. When the second solvent is water, it is suitable to include the high-silica zeolite in the pervaporation membrane 11 because of high resistance of the high-silica zeolite to hydrolysis. As the high-silica zeolite can be used HSZ (registered trademark) manufactured by Tosoh Corporation, HiSiv (registered trademark) manufactured by UNION SHOWA K.K., USKY manufactured by UNION SHOWA K.K., and Zeoal (registered trademark) manufactured by Nakamura Choukou Co., Ltd.

The filler 6 is, for example, in the shape of a particle. The term "shape of a particle" herein includes the shapes of a sphere, an ellipse, a flake, and a fiber. The average particle diameter of the fillers 6 is, for example, but not particularly limited to, 50 µm or less, preferably 20 µm or less, and more preferably 10 µm or less. The lower limit of the average particle diameter of the fillers 6 is, for example, 0.01 µm. The average particle diameter of the fillers 6 can be determined, for example, by the following method. First, a cross-section of the separation functional layer 1 is observed using a transmission electron microscope. The area of a specific filler 6 on the resulting electron microscope image is calculated by image processing. The diameter of a circle having the same area as the calculated area is regarded as the particle diameter (the diameter of the particle) of the specific filler 6. The particle diameter was calculated for any number (at least 50) of the fillers 6, and the average of the calculated values was regarded as the average particle diameter of the fillers 6.

The content of the filler 6 in the separation functional layer 1 is, for example, 10 wt % or more, preferably 30 wt % or more, and more preferably 40 wt % or more. The upper limit of the content of the filler 6 in the separation functional layer 1 is, for example, but not particularly limited to, 70 wt %.

The separation functional layer 1 has a thickness of, for example, 200 µm or less, preferably 100 µm or less, and more preferably 80 µm or less. The separation functional layer 1 may have a thickness of 1.0 µm or more, 10 µm or more, and 30 µm or more.

The separation functional layer 1 may have a microporous structure with an average pore diameter of less than 0.01 µm, but is preferably a dense layer having no pore on its surface. The separation functional layer 1 being a dense layer is suitable for allowing a lower alcohol to preferentially permeate therethrough and reducing permeation of an organic compound other than lower alcohols.

Examples of the porous support member 2 include: a nonwoven fabric; porous polytetrafluoroethylene; aromatic polyamide fiber; a porous metal; a sintered metal; porous ceramic; porous polyester; porous nylon; activated carbon fiber; latex; silicone; silicone rubber; a permeable (porous) polymer including at least one selected from the group consisting of polyvinyl fluoride, polyvinylidene fluoride, polyurethane, polypropylene, polyethylene, polystyrene, polycarbonate, polysulfone, polyether ether ketone, polyacrylonitrile, polyimide, and polyphenylene oxide; a metallic foam having an open cell or a closed cell; a polymer foam having an open cell or a closed cell; silica; a porous glass; and a mesh screen. The porous support member 2 may be a combination of two or more of these materials.

The porous support 2 may have an average pore diameter of, for example, 0.01 to 0.4 µm. The thickness of the porous support 2 is, for example, but not particularly limited to, 10 µm or more, preferably 50 µm or more, and more preferably 100 µm or more. The porous support 2 has a thickness of, for example, 300 µm or less and preferably 200 µm or less.

The material of the protective layer 3 is, for example, but not particularly limited to, a silicone resin. The material of the protective layer 3 may be the same as that of the matrix 5 of the separation functional layer 1. The thickness of the protective layer 3 is, for example, but not particularly limited to, 5 µm or more, preferably 10 µm or more, and more preferably 20 µm or more. The thickness of the protective layer 3 is, for example, 100 µm or less and preferably 50 µm or less.

The pervaporation membrane 11 can be produced, for example, by the following method. First, a coating liquid containing the materials of the separation functional layer 1 is prepared. The coating liquid may contain, along with the fillers 6, a dispersant for dispersing the fillers 6 in the coating liquid. When the coating liquid contains a silicone resin, the coating liquid may further contain a catalyst for curing the silicone resin. Next, the coating liquid is applied onto the porous support 2 to obtain a coating. The coating is then dried to obtain the separation functional layer 1.

Next, a coating liquid containing the material of the protective layer 3 is prepared. The coating liquid is applied onto the separation functional layer 1 to obtain a coating. The coating is then dried to obtain the protective layer 3. The pervaporation membrane 11 can be produced in this manner.

A separation factor of the pervaporation membrane 11 for the first solvent with respect to the second solvent is not particularly limited, and is preferably not too high. In one example, a separation factor α of the pervaporation membrane 11 for IPA with respect to water is, for example, 100 or less and preferably 60 or less. The lower limit of the separation factor α is, for example, but not particularly limited to, 5. The separation factor α can be measured by the following method. First, in a state in which a liquid mixture composed of IPA and water is in contact with one surface (e.g., a principal surface 11a, on the protective layer side, of the pervaporation membrane 11) of the separation membrane 11, a pressure in a space adjacent to the other surface (e.g., a principal surface 11b, on the porous support member side, of the pervaporation membrane 11) of the separation membrane 11 is decreased. A permeated fluid having permeated through the separation membrane 11 can thereby be obtained. The weight ratio of the water and the weight ratio of the IPA in the permeated fluid are measured. In the above procedure, the concentration of the IPA in the liquid mixture is 20 wt % when measured for the liquid mixture having a temperature of 20° C. The liquid mixture in contact with the pervaporation membrane 11 has a temperature of 40° C. The pressure in the space adjacent to the other surface of the pervaporation membrane 11 is decreased in such a manner that the pressure in the space is lower than an atmospheric pressure in a measurement environment by 100 kPa. The separation factor α can be calculated by the following formula. It should be noted that in the following formula, $X_A$ and $X_B$ are respectively the weight ratio of the IPA and the weight ratio of the water in the liquid mixture. $Y_A$ and $Y_B$ are respectively the weight ratio of the IPA and the weight ratio of the water in the permeated fluid having permeated through the pervaporation membrane 11.

Separation factor $\alpha=(Y_A/Y_B)/(X_A/X_B)$

As to the measurement conditions for the above separation factor α, the flux of the IPA permeating through the pervaporation membrane 11 is, for example, 0.005 (kg/m$^2$/hr) or more and preferably 0.01 (kg/m$^2$/hr) or more. The upper limit of the flux of the IPA permeating through the pervaporation membrane 11 is, for example, but not particularly limited to, 1.0 (kg/m$^2$/hr).

[Second Membrane Separation Device]

Figure 4:
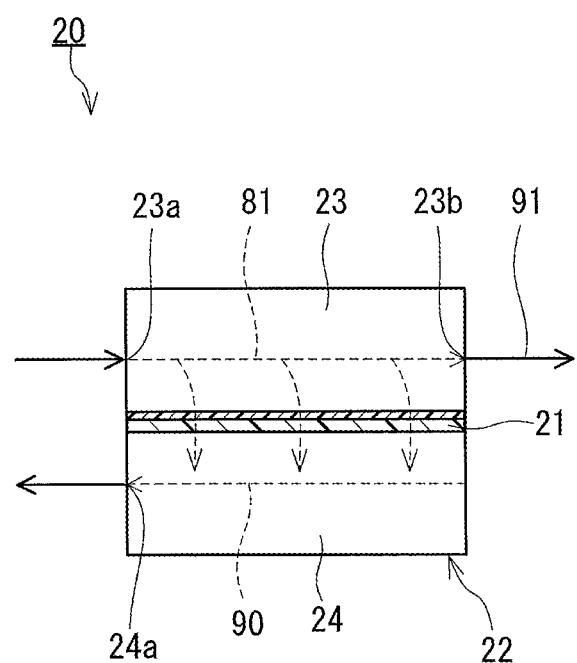
FIG. 4 is a schematic cross-sectional view showing an exemplary second membrane separation device.

As shown in FIG. 4, the second membrane separation device 20 includes a filtration membrane 21 and a tank 22. The tank 22 has a third chamber 23 and a fourth chamber 24. The filtration membrane 21 is placed in the tank 22. In the tank 22, the filtration membrane 21 separates the third chamber 23 and the fourth chamber 24. The filtration membrane 21 extends from one of a pair of wall surfaces of the tank 22 to the other.

The third chamber 23 has the inlet 23a and the outlet 23b. The fourth chamber 24 has the outlet 24a. The inlet 23a of the third chamber 23 is an opening for providing the first concentrated fluid 81 to the second membrane separation device 20. The outlet 24a of the fourth chamber 24 is an opening for discharging a second permeated fluid 90 obtained by allowing the first concentrated fluid 81 to permeate through the filtration membrane 21 from the second membrane separation device 20. The outlet 23b of the third chamber 23 is an opening for discharging the first concentrated fluid 81 (a second concentrated fluid 91) not having permeated through the filtration membrane 21 from the second membrane separation device 20. The inlet 23a, the outlet 23b, and the outlet 24a are arranged, for example, in wall surfaces of the tank 22.

The filtration membrane 21 is not particularly limited as long as the filtration membrane can allow the second solvent contained in the first concentrated fluid 81 to preferentially permeate therethrough. The filtration membrane 21 can be selected as appropriate according to the composition of the impurity, and examples thereof include an RO membrane, a nanofiltration membrane (NF membrane), an ultrafiltration membrane (UF membrane), a microfiltration membrane (MF membrane), and an ion-exchange membrane. The filtration membrane 21 is preferably an RO membrane or a NF membrane. RO and NF membranes are suitable for reducing permeation of the impurity including a low-molecular compound. When the impurity includes salt, an ion-exchange membrane may be used as the filtration membrane 21.

Herein, the term "RO membrane" refers to a membrane whose sodium chloride removal rate determined by filtering a test solution having a sodium chloride concentration of 2000 mg/L at an operating pressure of 1.5 MPa is 93% or more. The term "NF membrane" refers to a membrane whose sodium chloride removal rate determined by filtering a test solution having a sodium chloride concentration of 2000 mg/L at an operating pressure of 1.5 MPa is 5% or more and less than 93%.

NF and RO membranes each commonly include a dense layer and a porous support supporting the dense layer. The thickness of the dense layer is, for example, but not particularly limited to, 0.001 to 2 μm and preferably 0.005 to 1 μm. Any of the porous supports described above can be used as the porous support supporting the dense layer.

The material of the dense layer is not particularly limited, and, for example, a polymeric material such as a modified polyethersulfone, a cellulose ester (e.g., cellulose acetate), a polyamide (e.g., an aromatic polyamide), a polyester, a polyimide, a vinyl polymer, a polyethersulfone, and an ethylene-vinyl alcohol copolymer can be used.

The thickness of the filtration membrane 21 is not particularly limited, and is preferably 10 to 200 μm and more preferably 20 to 75 μm.

The molecular weight cut-off of the filtration membrane 21 is, for example, 10000 or less, preferably 5000 or less, and more preferably 1000 or less. The lower limit of the molecular weight cut-off of the filtration membrane 21 is not particularly limited, and is, for example, 100. The molecular weight cut-off of the filtration membrane 21 can be determined by a known method. One example of the method for determining the molecular weight cut-off of the filtration membrane 21 is as follows. First, a plurality of polyethylene glycols whose average molecular weights are different from each other and whose molecular weight distributions are monodisperse are prepared. An aqueous solution containing one of the plurality of polyethylene glycols at a concentration of 5000 ppm is supplied to a membrane surface of the filtration membrane 21 at a temperature of 25° C. and a pressure of 4 kg/cm$^2$. A polyethylene glycol rejection rate can be measured thereby for the polyethylene glycol. Rejection rates are measured for the other polyethylene glycols by the same method. A molecular weight cut-off curve showing relations between the obtained rejection rates and the average molecular weights of the polyethylene glycols is created. The average molecular weight of a polyethylene glycol rejected at a rejection rate of 90% is determined on the basis of the molecular weight cut-off curve. The determined average molecular weight can be regarded as a molecular weight cut-off of the filtration membrane 21.

[Method for Purifying Mixture]

In the present embodiment, a method for purifying the mixture 70 includes a first separation step in which the first membrane separation device 10 is used. The first separation step is, for example, a separation step initially performed for a washing solution (the mixture 70) having been used to wash a washing target. The first separation step is performed, for example, in the following manner. First, the mixture 70 is supplied to the first chamber 13 of the first membrane separation device 10 via the mixture supply passage 30. This brings the mixture 70 into contact with the one surface of the pervaporation membrane 11. The amount of the mixture 70 supplied is not particularly limited, and is determined according to the processing capacity of the first membrane separation device 10. The amount of the mixture 70 supplied is, for example, 0.5 kg/hr to 500 kg/hr. Before supplied to the first chamber 13, the mixture 70 may be heated by the heat exchanger 60 provided to the mixture supply passage 30. The temperature of the mixture 70 supplied to the first chamber 13 is, for example, 30° C. or higher. The upper limit of the temperature of the mixture 70 is, for example, 75° C.

Next, in a state where the liquid mixture 70 is in contact with the one surface of the pervaporation membrane 11, the pressure in the space adjacent to the other surface of the pervaporation membrane 11 is decreased. Specifically, the pressure in the second chamber 14 is decreased through the outlet 14a. The pressure in the second chamber 14 can be decreased using the pump 52 provided to the first discharge passage 32. The pressure in the second chamber 14 is decreased in such a manner that the pressure in the space in the second chamber 14 is lower than an atmospheric pressure in a measurement environment by, for example, 10 kPa or more, preferably 50 kPa or more, and more preferably 80 kPa or more.

The first permeated fluid 80 having a low concentration of the impurity can be obtained on the other surface of the pervaporation membrane 11 by decreasing the pressure in the second chamber 14. In other words, the first permeated fluid 80 is supplied to the second chamber 14. The first permeated fluid 80 may be a gas or a liquid in the second chamber 14. The first permeated fluid 80 is discharged outside the first membrane separation device 10 via the outlet 14a. The first permeated fluid 80 discharged outside the first membrane separation device 10 is, for example, cooled by the heat exchanger 62 provided to the first discharge passage 32. The gaseous first permeated fluid 80 is liquefied thereby. The temperature of the first permeated fluid 80 cooled by the heat exchanger 62 is, for example, 10° C. or lower and preferably 0° C. or lower.

On the other hand, the concentration of the impurity in the mixture 70 gradually increases from the inlet 13a toward the outlet 13b in the first chamber 13. The mixture 70 processed in the first chamber 13 (the first concentrated fluid 81) is discharged outside the first membrane separation device 10 via the outlet 13b. The first concentrated fluid 81 is typically a liquid.

As described above, the pervaporation membrane 11 of the first membrane separation device 10 can allow the first solvent contained in the mixture 70 to preferentially permeate therethrough. Accordingly, the first permeated fluid 80 obtained by the first separation step has a lower concentration of the impurity than that in the mixture 70. By the first separation step, the concentration of the impurity in the first permeated fluid 80 can be decreased to, for example, 100 ppm or less, in some cases, 50 ppm or less, and even 10 ppm or less. In the first separation step, an impurity removal rate calculated by the following formula is, for example, 80% or more, preferably 90% or more, more preferably 95% or more, and even more preferably 99% or more.

Impurity removal rate (%)={(concentration (ppm) of impurity in mixture−concentration (ppm) of impurity in first permeated fluid)/concentration (ppm) of impurity in mixture}×100

The first permeated fluid 80 obtained by the first separation step has a higher concentration of the first solvent than that in the mixture 70. A ratio of the concentration (wt %) of the first solvent in the first permeated fluid 80 to the concentration (wt %) of the first solvent in the mixture 70 is, for example, but not particularly limited to, 1.5 to 5.0.

The first concentrated fluid 81 has a higher concentration of the impurity than that in the mixture 70 and has a lower concentration of the first solvent than that in the mixture 70. A ratio of the concentration (ppm) of the impurity in the first concentrated fluid 81 to the concentration (ppm) of the impurity in the mixture 70 is, for example, 1.1 or more and preferably 1.2 or more. A ratio of the concentration (wt %) of the first solvent in the first concentrated fluid 81 to the concentration (wt %) of the first solvent in the mixture 70 is, for example, 0.5 or less and preferably 0.2 or less.

As described above, the first permeated fluid 80 having a lower concentration of the impurity than that in the mixture 70 and a higher concentration of the first solvent than that in the mixture 70 can be obtained by the first separation step. The first separation step requires a smaller amount of energy than a distillation method and does not require an absorbing material, which is used in an absorption method. As just described, the mixture 70 containing a plurality of solvents can be efficiently purified by the purification method including the first separation step, compared to the conventional purification methods.

In order to obtain the first permeated fluid 80 having a low concentration of the impurity when the first solvent is the lower alcohol and the second solvent is water, the pervaporation membrane 11 used in the first separation step needs to allow the lower alcohol contained in the mixture 70 to preferentially permeate therethrough. Patent Literature 1 states (in FIG. 1 and the paragraphs 0027 and 0028) that a washing solution discharged from a washing device is supplied to a concentrator to increase the concentration of an alcohol in the washing solution by a pervaporation method. However, according to the paragraph 0047 of Patent Literature 1, the washing solution concentrated using the concentrator is contaminated by an impurity derived from a washing target. From these descriptions, it can be understood that a pervaporation membrane included in the concentrator of Patent Literature 1 is a separation membrane allowing water, rather than an alcohol, to preferentially permeate therethrough. In Patent Literature 1, a permeated fluid having permeated through the pervaporation membrane is not reused and delivered to a waste solution tank.

The purification method of the present embodiment further includes, for example, a second separation step in which the second membrane separation device 20 is used. The second separation step is performed, for example, in the following manner for the first concentrated fluid 81 obtained by the first separation step. First, the first concentrated fluid 81 is supplied to the third chamber 23 of the second membrane separation device 20 via the concentrated fluid supply passage 34. This brings the first concentrated fluid 81 into contact with one surface of the filtration membrane 21, and thereby the second permeated fluid 90 having a low concentration of the impurity can be obtained on the other surface side (in the fourth chamber 24) of the filtration membrane 21.

In the second separation step, the third chamber 23 may be filled with the first concentrated fluid 81. Moreover, the fourth chamber 24 may be filled with the second solvent (or the second permeated fluid 90). In the second separation step, the first concentrated fluid 81 filling the third chamber 23 may be pressurized using the pump 54 provided to the concentrated fluid supply passage 34. The pressure in the third chamber 23 is, for example, 10 bar or more, preferably 20 bar or more, and more preferably 40 bar or more. The pressure in the third chamber 23 is, for example, 100 bar or less.

The concentration of the impurity in the first concentrated fluid 81 gradually increases from the inlet 23a toward the outlet 23b in the third chamber 23. The first concentrated fluid 81 processed in the third chamber 23 (the second concentrated fluid 91) is discharged outside the second membrane separation device 20 via the outlet 23b. The second concentrated fluid 91 is discharged from the discharge outlet 46 via the third discharge passage 37.

As described above, the filtration membrane 21 of the second membrane separation device 20 can allow the second solvent contained in the first concentrated fluid 81 to preferentially permeate therethrough. Accordingly, the second permeated fluid 90 obtained by the second separation step has a lower concentration of the impurity than that in the first concentrated fluid 81. By the second separation step, the concentration of the impurity in the second permeated fluid 90 can be decreased to, for example, 100 ppm or less, in some cases, 50 ppm or less, and even 10 ppm or less. In the second separation step, the impurity removal rate calculated by the same method as for the impurity removal rate in the first separation step is, for example, 80% or more, preferably 90% or more, more preferably 95% or more, and even more preferably 99% or more. On the other hand, the second concentrated fluid 91 has a higher concentration of the impurity than that in the first concentrated fluid 81. A ratio of the concentration (ppm) of the impurity in the second concentrated fluid 91 to the concentration (ppm) of the impurity in the first concentrated fluid 81 is, for example, 1.1 or more and preferably 1.2 or more.

The purification method of the present embodiment further includes, for example, a mixing step of mixing the first permeated fluid 80 and the second permeated fluid 90. The mixing step can be performed by delivering the second permeated fluid 90 to the joining point 40 in the first discharge passage 32 via the second discharge passage 36. The amount of a fluid to be disposed of can be greatly decreased by further performing the second separation step and the mixing step for the first concentrated fluid 81 obtained by the first separation step instead of disposing of the first concentrated fluid 81.

It is theoretically possible to change the order of the first separation step and the second separation step. However, when the first solvent is the lower alcohol and the second solvent is water, changing the order of the first separation step and the second separation step means that membrane separation using the filtration membrane is performed for the mixture 70 having a relatively high concentration of the lower alcohol and exhibiting a high osmotic pressure, and that needs to pressurize the mixture 70 to a very high pressure level. Furthermore, the amount of a fluid to be disposed of is increased by performing the first separation step after the second separation step because the amount of the concentrated fluid obtained by the first separation step is relatively large. As described above, the second separation step is preferably performed after the first separation step for efficient purification of the mixture 70.

The purification method of the present embodiment may further include an adjustment step of adding a raw material including at least one selected from the group consisting of the first solvent and the second solvent to the first permeated fluid 80, the second permeated fluid 90, or the fluid mixture of the first permeated fluid 80 and the second permeated fluid 90 to adjust the concentrations of the first solvent and the second solvent in the fluid. The adjustment step can be performed, for example, by supplying the above raw material to the first discharge passage 32 or the second discharge passage 36 via the raw material supply passage 38. The adjustment step may be performed before the mixing step, but is preferably performed after the mixing step. That is, in the adjustment step, the above raw material is preferably added to the fluid mixture of the first permeated fluid 80 and the second permeated fluid 90. Herein, a fluid mixture containing the first solvent and the second solvent at concentrations adjusted through the mixing step and the adjustment step is sometimes referred to as "purification product".

In the adjustment step, the composition and weight of the raw material added to the fluid can be determined as appropriate according to the concentrations of the first solvent and the second solvent in the purification product and the weight of the purification product. The concentrations of the first solvent and the second solvent in the purification product and the weight of the purification product may be the same as or different from those in the mixture 70.

By the purification method of the present embodiment, the concentration of the impurity in the purification product can be decreased to, for example, 100 ppm or less, in some cases, 50 ppm or less, and even 10 ppm or less. In the purification method of the present embodiment, a rate (first solvent recovery rate) of the sum of the weight of the first solvent contained in the first permeated fluid 80 and the weight of the first solvent contained in the second permeated fluid 90 to the weight of the first solvent contained in the mixture 70 is, for example, but not particularly limited to, 75% or more, preferably 85% or more, and more preferably 90% or more. A rate (the second solvent recovery rate) of the sum of the weight of the second solvent contained in the first permeated fluid 80 and the weight of the second solvent contained in the second permeated fluid 90 to the weight of the second solvent contained in the mixture 70 is, for example, but not particularly limited to, 50% or more and preferably 70% or more. The purification product obtained by the purification method of the present embodiment is reused, for example, for a given application (e.g., as a washing solution). In another aspect, the present invention provides a solvent manufacturing method including the above purification method. A solvent obtained by this manufacturing method contains, for example, the first solvent and typically contains the first solvent and the second solvent.

The first membrane separation device 10 and the second membrane separation device 20 included in the purification system 100 is suitable for a flow-type (continuous-type) membrane separation method. However, these membrane separation devices may be used for a batch-type membrane separation method.

[Modification of First Membrane Separation Device]

Figure 5:
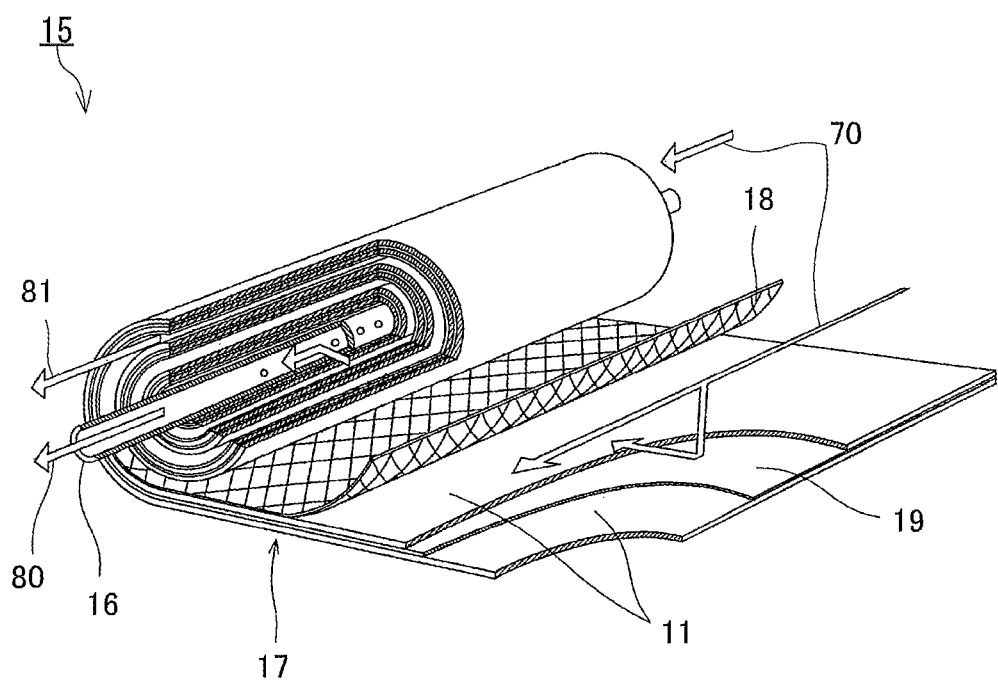
FIG. 5 is a schematic cross-sectional view showing another exemplary first membrane separation device.

In the purification system 100, the first membrane separation device 10 may be a spiral membrane element as shown in FIG. 5. A first membrane separation device 15 of FIG. 5 includes a central tube 16 and a laminate 17. The laminate 17 includes the pervaporation membrane 11.

The central tube 16 has a cylindrical shape. The central tube 16 has a surface with a plurality of holes or slits to allow the first permeated fluid 80 to flow into the central tube 16. Examples of the material of the central tube 16 include: resins such as an acrylonitrile-butadiene-styrene copolymer resin (ABS resin), a polyphenylene ether resin (PPE resin), and a polysulfone resin (PSF resin); and metals such as stainless steel and titanium. The central tube 16 has an inner diameter in a range of, for example, 20 to 100 mm.

The laminate 17 further includes, for example, a supply-side flow passage material 18 and a permeation-side flow passage material 19 in addition to the pervaporation membrane 11. The laminate 17 is wound around the central tube 16. The first membrane separation device 15 may further include an exterior material (not shown).

For example, a resin net, woven fabric, or knitted fabric composed of polyethylene, polypropylene, polyethylene terephthalate (PET), polyphenylene sulfide (PPS), or an ethylene-chlorotrifluoroethylene copolymer (ECTFE) can be used as the supply-side flow passage material 18 and the permeation-side flow passage material 19.

Membrane separation in which the first membrane separation device 15 is used is performed, for example, by the following method. First, the mixture 70 is supplied to one end of the wound laminate 17. The pressure in the space inside the central tube 16 is decreased. The first permeated fluid 80 having permeated through the pervaporation membrane 11 of the laminate 17 thereby moves into the central tube 16. The first permeated fluid 80 is discharged outside via the center tube 16. The mixture 70 processed by the first membrane separation device 15 (the first concentrated fluid 81) is discharged outside from the other end of the wound laminate 17.

In the purification system 100, the second membrane separation device 20 may be a spiral membrane element having the same configuration as that of the first membrane separation device 15.

<Modification of Purification System>

Figure 6:
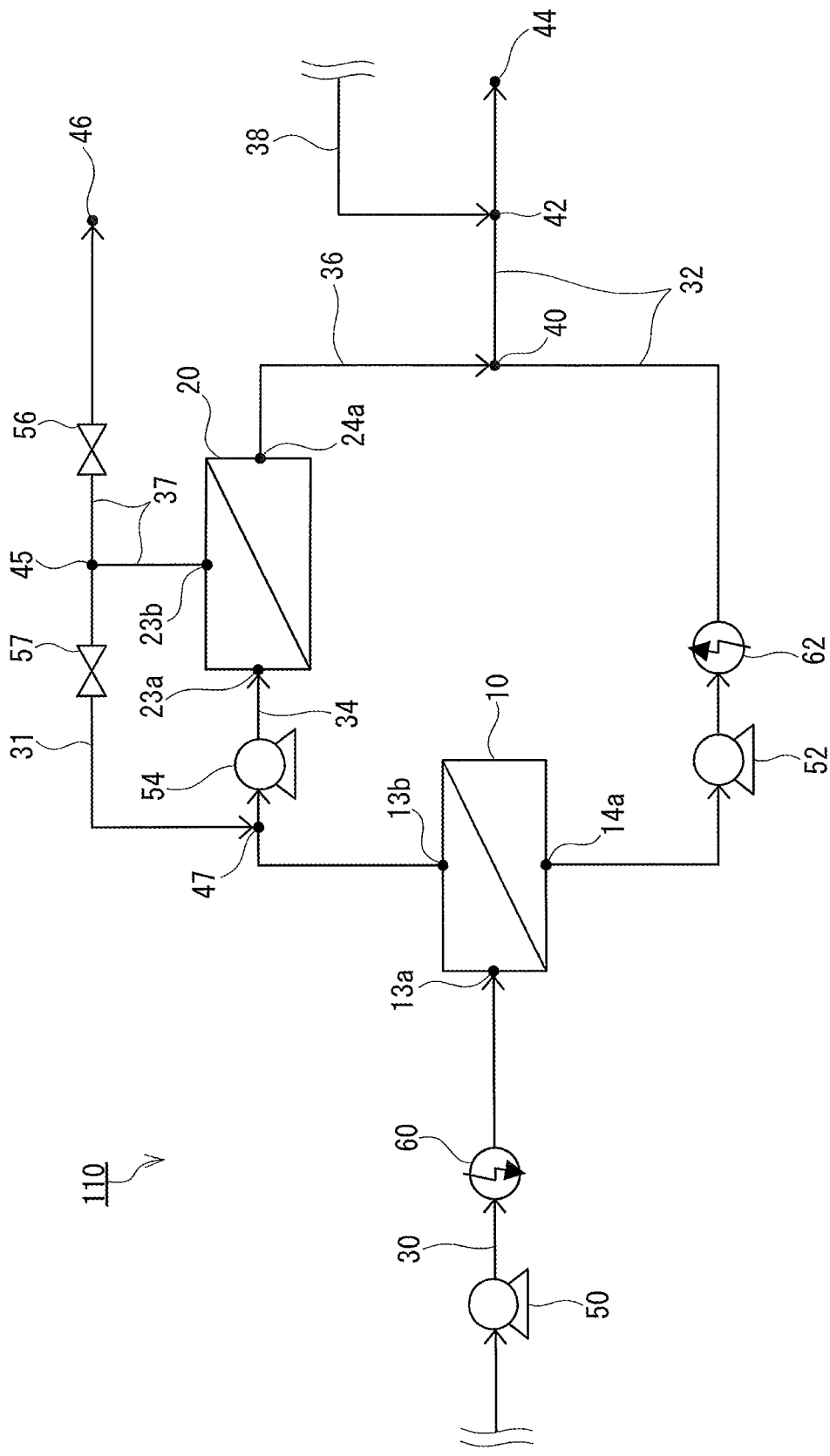
FIG. 6 is a configuration diagram showing another exemplary purification system.

The purification system 100 may further have a configuration for delivering a portion of the second concentrated fluid 91 discharged from the second membrane separation device 20 to the concentrated fluid supply passage 34. A purification system 110 of the present embodiment shown in FIG. 6 further includes a recycle passage 31, a valve 56, and a valve 57. Except for these, the structure of the purification system 110 of the present embodiment is the same as that of the purification system 100.

Therefore, the elements common between the purification system 100 and the purification system 110 of the present embodiment are denoted by the same reference characters, and the description of such elements may be omitted. That is, the description of each of the following embodiments is applicable to the other embodiment unless technical inconsistency occurs. Furthermore, the features of the embodiments may be combined with each other unless technical inconsistency occurs.

The recycle passage 31 is connected to both the third discharge passage 37 and the concentrated fluid supply passage 34. Specifically, the recycle passage 31 branches at a branch point 45 in the third discharge passage 37 and joins the concentrated fluid supply passage 34 at a joining point 47. The recycle passage 31 is a passage configured to deliver a portion of the second concentrated fluid 91 discharged from the second membrane separation device 20 to the concentrated fluid supply passage 34. With the recycle passage 31, the portion of the second concentrated fluid 91 can be mixed with the first concentrated fluid 81 in the concentrated fluid supply passage 34. The composition of the second concentrated fluid 91 is almost the same as that of the first concentrated fluid 81 discharged from the first membrane separation device 10, except for the concentrations of the components. Therefore, for convenience, the fluid mixture of the portion of the second concentrated fluid 91 and the first concentrated fluid 81 is herein also referred to as "first concentrated fluid 81" sometimes.

The joining point 47 is located, for example, between the first membrane separation device 10 and the pump 54. The concentrated fluid supply passage 34 may further be provided with a tank, and the recycle passage 31 may be connected to the tank. In this case, the tank provided to the concentrated fluid supply passage 34 can be regarded as the joining point 47.

The valve 56 is provided to the third discharge passage 37 between the branch point 45 and the discharge outlet 46. The valve 57 is provided to the recycle passage 31. Flow rate adjusting valves can be used as the valves 56 and 57. For example, a ratio between the flow rate of the second concentrated fluid 91 delivered from the third discharge passage 37 to the recycle passage 31 and the flow rate of the second concentrated fluid 91 discharged from the discharge outlet 46 can be adjusted as appropriate by adjusting the degree of opening of each of the valves 56 and 57. The purification system 110 may include a pump, instead of the valves 56 and 57, for adjusting the flow rate of the second concentrated fluid 91 delivered from the third discharge passage 37 to the recycle passage 31.

In the present embodiment, the purification method further includes, for example, a recycle step of delivering the portion of the second concentrated fluid 91 to the concentrated fluid supply passage 34 via the recycle passage 31. By the recycle step, the portion of the second concentrated fluid 91 is mixed with the first concentrated fluid 81 at the joining point 47. The fluid mixture obtained at the joining point 47 is delivered to the second membrane separation device 20. The second solvent recovery rate can be easily improved by the recycle step.

In the recycle step, a rate (recycling rate A) of the flow rate (kg/hr) of the second concentrated fluid 91 passing through the recycle passage 31 to the flow rate (kg/hr) of the second concentrated fluid 91 having just been discharged from the second membrane separation device 20 can be set as appropriate according to a desired second solvent recovery rate, and is, for example, 68% to 98%.

<Another Modification of Purification System>

Figure 7:
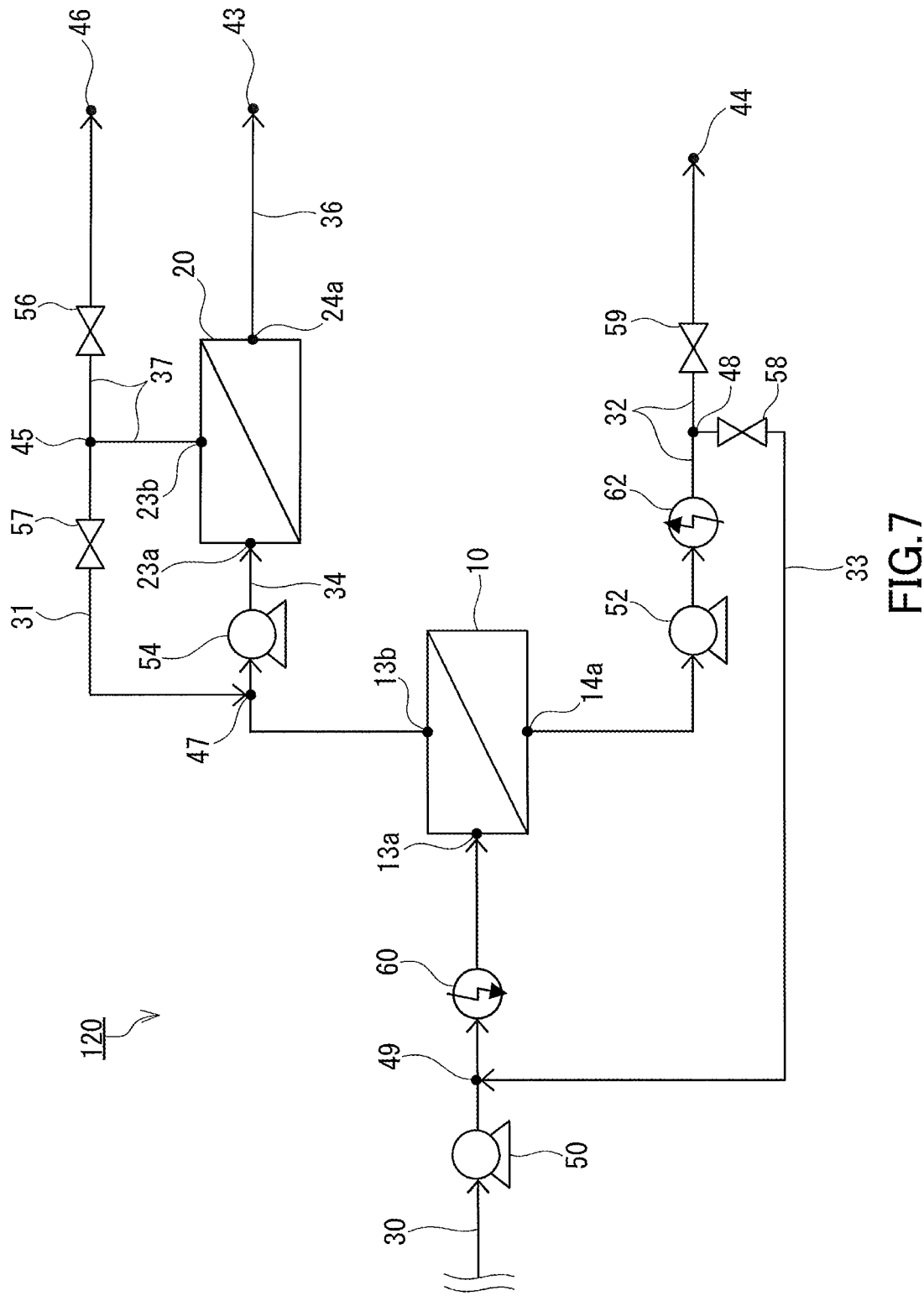
FIG. 7 is a configuration diagram showing yet another exemplary purification system.

The purification system 110 may further have a configuration for delivering a portion of the first permeated fluid 80 discharged from the first membrane separation device 10 to the mixture supply passage 30. A purification system 120 of the present embodiment as shown in FIG. 7 further includes a recycle passage 33, a valve 58, and a valve 59. In the purification system 120, the second discharge passage 36 does not join the first discharge passage 32. Moreover, the purification system 120 does not include the raw material supply passage 38. Except for these, the structure of the purification system 120 of the present embodiment is the same as that of the purification system 110. Herein, the recycle passage 33 is sometimes referred to as "first recycle passage", and the recycle passage 31 is sometimes referred to as "second recycle passage".

A first recycle passage 33 is connected to both the first discharge passage 32 and the mixture supply passage 30.

Specifically, the first recycle passage 33 branches at a branch point 48 in the first discharge passage 32 and joins the mixture supply passage 30 at a joining point 49. The first recycle passage 33 is a passage configured to deliver the portion of the first permeated fluid 80 discharged from the first membrane separation device 10 to the mixture supply passage 30. With the first recycle passage 33, the portion of the first permeated fluid 80 can be mixed with the mixture 70 in the mixture supply passage 30. The composition of the first permeated fluid 80 is almost the same as that of the mixture 70 supplied to the first membrane separation device 10, except for the concentrations of the components. Therefore, for convenience, the fluid mixture of the portion of the first permeated fluid 80 and the mixture 70 is herein also referred to as "mixture 70" sometimes.

The branch point 48 is located, for example, downstream of the heat exchanger 62, specifically, for example, between the heat exchanger 62 and the discharge outlet 44. The joining point 49 is located, for example, downstream of the pump 50, specifically, for example, between the pump 50 and the heat exchanger 60. The mixture supply passage 30 may further be provided with a tank, and the first recycle passage 33 may be connected to the tank. In this case, the tank provided to the mixture supply passage 30 can be regarded as the joining point 49.

The valve 58 is provided to the first recycle passage 33. The valve 59 is provided to the first discharge passage 32 between the branch point 48 and the discharge outlet 44. Flow rate adjusting valves can be used as the valves 58 and 59. For example, a ratio between the flow rate of the first permeated fluid 80 delivered from the first discharge passage 32 to the first recycle passage 33 and the flow rate of the first permeated fluid 80 discharged from the discharge outlet 44 can be adjusted as appropriate by adjusting the degree of opening of each of the valves 58 and 59. The purification system 120 may include a pump, instead of the valves 58 and 59, for adjusting the flow rate of the first permeated fluid 80 delivered from the first discharge passage 32 to the first recycle passage 33.

As described above, in the purification system 120, the second discharge passage 36 does not join the first discharge passage 32. In the present embodiment, an opening (a discharge outlet 43) for discharging the second permeated fluid 90 from the second discharge passage 36 is arranged in the second discharge passage 36.

In the present embodiment, the purification method further includes, for example, a recycle step of delivering the portion of the first permeated fluid 80 to the mixture supply passage 30 via the first recycle passage 33. By the recycle step, the portion of the first permeated fluid 80 is mixed with the mixture 70 at the joining point 49. The fluid mixture obtained at the joining point 49 is delivered to the first membrane separation device 10. Herein, the recycle step in which the first recycle passage 33 is used is sometimes referred to as "first recycle step", and the recycle step in which the second recycle passage 31 is used is sometimes referred to as "second recycle step".

By the first recycle step, the concentration of the first solvent in the first permeated fluid 80 can be easily increased without greatly increasing the energy needed to operate the purification system 120 and without employing a membrane having high separation performance as the pervaporation membrane 11 in the first membrane separation device 10. The first permeated fluid 80 obtained by the purification method of the present embodiment has a relatively high concentration of the first solvent and can be reused for various applications.

In the first recycle step, a rate (recycling rate B) of the flow rate (kg/hr) of the first permeated fluid 80 permeating through the recycle passage 33 to the flow rate (kg/hr) of the first permeated fluid 80 having just been discharged from the first membrane separation device 10 can be set as appropriate according to desired composition of the first permeated fluid 80, and is, for example, 5% to 60%.

In the present embodiment, the purification method does not include the mixing step of mixing the first permeated fluid 80 and the second permeated fluid 90. That is, in the present embodiment, the first permeated fluid 80 and the second permeated fluid 90 are separately recovered. Specifically, the first permeated fluid 80 is discharged from the discharge outlet 44 via the first discharge passage 32. The second permeated fluid 90 is discharged from the discharge outlet 43 via the second discharge passage 36.

EXAMPLES

Hereinafter, the present invention will be described in more detail by way of Examples and Comparative Examples, but the present invention is not limited to these examples.

Measurement Example 1

First, a pervaporation membrane was produced by the following method. A coating liquid was prepared by mixing 2.810 kg (solids concentration: 30 wt %) of a silicone resin (YSR3022 manufactured by Momentive Performance Materials Japan LLC.), 4.778 kg of toluene, 0.843 kg of a high-silica zeolite (HiSiv 3000 manufactured by UNION SHOWA K.K.), 0.004 kg of a dispersant (MALIALIM AWS-0851 manufactured by NOF CORPORATION), 0.028 kg of a silicone curing catalyst (YC6831 manufactured by Momentive Performance Materials Japan LLC.), and 0.084 kg of acetylacetone as a curing retardant. Next, the coating liquid was applied onto a porous support (RS-50 manufactured by Nitto Denko Corporation) having a thickness of 150 μm to obtain a coating (thickness: 500 μm). The coating was heated at 90° C. for 4 minutes and then dried to produce a separation functional layer having a thickness of 67 μm. The weight ratio between the silicone resin and the high-silica zeolite was 50:50 in the separation functional layer.

Next, a coating liquid was prepared by mixing 4.617 kg (solids concentration: 30 wt %) of a silicone resin (YSR3022 manufactured by Momentive Performance Materials Inc.), 2.308 kg of toluene, 0.046 kg of a silicone curing catalyst (YC6831 manufactured by Momentive Performance Materials Inc.), and 0.138 kg of acetylacetone as a curing retardant. Next, the coating liquid was applied onto the separation functional layer to obtain a coating (thickness: 200 μm). The coating was heated at 90° C. for 4 minutes and then dried to produce a protective layer having a thickness of 33 μm. A pervaporation membrane was thus obtained.

A spiral membrane element as shown in FIG. 5 was produced using the pervaporation membrane. The membrane element had a length of 300 mm and an outer diameter of 63 mm. The permeation-side flow passage material in the membrane element had a thickness of 250 μm. The supply-side flow passage material had a thickness of 300 μm. The pervaporation membrane in the membrane element had a membrane area of 0.86 m².

Next, a purification test was performed for a mixture composed of IPA, water, and impurities using the membrane element. The concentration of the IPA in the mixture to be purified was 6.3 wt %. The impurities contained in the mixture were triethylamine (TEA), N,N-dimethylformamide (DMF), camphorsulfonic acid (CSA), and m-phenylenediamine (MPD), and the total concentration of the impurities was 889 ppm. Table 1 shows the concentrations of the impurities.

In the purification test, the above mixture was supplied to the membrane element at a flow rate of 8.3 g/min (0.498 kg/hr). The mixture supplied to the membrane element had a temperature of 40° C. The pressure in the space inside the central tube of the membrane element was decreased in such a manner that the pressure in the space was lower than an atmospheric pressure in a measurement environment by 100 kPa. A gaseous permeated fluid was obtained thereby from the membrane element. The gaseous permeated fluid was cooled using −196° C. liquid nitrogen to liquefy the permeated fluid. The composition of the liquid permeated fluid was analyzed by gas chromatography. The concentration of the IPA in the permeated fluid was 19.3 wt %. The flow rate of the IPA having permeated through the pervaporation membrane was 0.0160 kg/hr, and the flow rate of the water having permeated through the pervaporation membrane was 0.0669 kg/hr. Table 1 shows the concentrations of the impurities contained in the permeated fluid.

TABLE 1

| Impurities | Mixture to be purified Concentration (ppm) | Permeated fluid Concentration (ppm) |
| --- | --- | --- |
| TEA | 260 | 0.67 |
| DMF | 22 | 1.9 |
| CSA | 509 | <0.053 |
| MPD | 98 | 0.037 |
| Total | 889 | <2.66 |

As shown in Table 1, the total concentration of the impurities in the permeated fluid obtained from the membrane element was about 2.5 ppm, which reveals that the membrane element can greatly decrease the concentration of the impurities. The impurity removal rate exhibited by the membrane element was very high, namely 99.7%.

Measurement Example 2

<First Separation Step>

First, a pervaporation membrane was produced by the following method. A coating liquid was prepared by mixing 1.650 kg (solids concentration: 30 wt %) of a silicone resin (YSR3022 manufactured by Momentive Performance Materials Japan LLC.), 2.805 kg of toluene, 0.495 kg of a high-silica zeolite (HiSiv 3000 manufactured by UNION SHOWA K.K.), 0.0495 kg of a silicone curing catalyst (YC6831 manufactured by Momentive Performance Materials Japan LLC.), and 0.0495 kg of acetylacetone as a curing retardant. Next, the coating liquid was applied onto a porous support (RS-50 manufactured by Nitto Denko Corporation) having a thickness of 150 μm to obtain a coating (thickness: 500 μm). The coating was heated at 90° C. for 4 minutes and then dried to produce a separation functional layer having a thickness of 50 μm. The weight ratio between the silicone resin and the high-silica zeolite was 50:50 in the separation functional layer. A pervaporation membrane was thus obtained.

A spiral membrane element as shown in FIG. 5 was produced using the pervaporation membrane. The membrane element had a length of 300 mm and an outer diameter of 63 mm. The permeation-side flow passage material in the membrane element had a thickness of 250 μm. The supply-side flow passage material had a thickness of 850 μm. The pervaporation membrane in the membrane element had a membrane area of 0.4 m².

Next, the first separation step was performed for a mixture composed of IPA, water, and impurities using 30 thus-obtained membrane elements connected in series. The concentration of the IPA in the mixture to be purified was 4.1 wt %. The impurities contained in the mixture were triethylamine (TEA), sodium lauryl sulfate (SLS), camphorsulfonic acid (CSA), p-toluenesulfonic acid (p-TSA), triethanolamine (TEtA), and m-phenylenediamine (MPD), and the total concentration of the impurities was 525 ppm. Table 2 shows the concentrations of the impurities.

In the first separation step, the above mixture was supplied to the membrane elements at a flow rate of 2.5 kg/hr. The mixture supplied to the membrane elements had a temperature of 40° C. The pressure in the space inside the central tube of each membrane element was decreased in such a manner that the pressure in the space was lower than an atmospheric pressure in a measurement environment by 100 kPa. A gaseous permeated fluid (first permeated fluid) was obtained thereby from the membrane elements. The gaseous permeated fluid was cooled using −7° C. chiller water to liquefy the permeated fluid. The composition of the liquid permeated fluid was analyzed by gas chromatography. The concentration of the IPA in the permeated fluid was 14.4 wt %. The flow rate of the IPA having permeated through the pervaporation membrane was 0.0864 kg/hr, and the flow rate of the water having permeated through the pervaporation membrane was 0.5136 kg/hr. Furthermore, the composition of a fluid (first non-permeated fluid) not having permeated through the pervaporation membrane was analyzed by gas chromatography. The total flow rate of the first non-permeated fluid was 1.9 kg/hr. In the first non-permeated fluid, the flow rate of the IPA was 0.0076 kg/hr and the flow rate of water was 18.9924 kg/hr. Table 2 shows the concentrations of the impurities contained in the permeated fluid and the non-permeated fluid. As can be understood from the results in Table 2, a permeated fluid containing a concentrated IPA and having a decreased concentration of the impurities was obtained by the first separation step in which the pervaporation membrane was used.

TABLE 2

| Impurities | Mixture to be purified Concentration (ppm) | First permeated fluid Concentration (ppm) | First non-permeated fluid Concentration (ppm) |
| --- | --- | --- | --- |
| TEA | 96 | 13 | 110 |
| SLS | Less than quantitation limit | Less than quantitation limit | Less than quantitation limit |
| CSA | 250 | 12 | 300 |
| p-TSA | 8.4 | 0.23 | 11 |
| TEtA | 130 | Less than quantitation limit | 110 |
| MPD | 41 | 2.1 | 37 |
| Total | 525 | 27.3 | 568 |

<Second Separation Step>

Next, the second separation step was performed in the following manner for the first non-permeated fluid obtained in the first separation step. First, a batch-type membrane separation device C40-B (manufactured by Nitto Denko Corporation) provided with an RO membrane (SWC5 manufactured by Nitto Denko Corporation) was prepared. The RO membrane provided had a membrane area of 34.2c m². An amount of 300 ml of the first non-permeated fluid was supplied to this membrane separation device. The temperature of the first non-permeation fluid was room temperature (25° C.). Next, the second separation step was performed by supplying nitrogen gas into the membrane separation device to apply a pressure of 22.4 bar to the first non-permeated fluid. During the second separation step, the first non-permeated fluid was being stirred using a magnetic stirrer provided to the membrane separation device to reduce concentration polarization of the first non-permeated fluid supplied. An amount of 225 ml of a liquid permeated fluid (second permeated fluid) was obtained by the second separation step. Since the IPA was sufficiently removed from the mixture by the first separation step, the concentration of the IPA in the first non-permeated fluid was relatively low and the osmotic pressure of the first non-permeated fluid was sufficiently low. Therefore, the second separation step sufficiently progressed just by the application of a pressure of 22.4 bar to the first non-permeated fluid, and a waste solution (second non-permeated fluid) was able to be easily reduced in volume.

Next, the concentration of the IPA in each fluid obtained by the second separation step was analyzed by gas chromatography. The concentration of the IPA in the second permeated fluid was less than 0.1 wt %, and the concentration of the IPA in the second non-permeated fluid was 1.0 wt %. Table 3 shows the concentrations of the impurities contained in the second permeated fluid. As can be understood from Table 3, because the concentration of the IPA and those of the impurities in the second permeated fluid are sufficiently low, the second permeated fluid can be used to dilute the first permeated fluid.

TABLE 3

| Impurities | Second permeated fluid Concentration (ppm) |
|---|---|
| TEA | 0.44 |
| SLS | Less than quantitation limit |
| CSA | 0.83 |
| p-TSA | 0.043 |
| TEtA | Less than quantitation limit |
| MPD | 0.46 |
| Total | 1.77 |

Calculation Example 1

Next, a material balance was calculated for a purification system as shown in FIG. 1. A process simulator, Symmetry (manufactured by Schlumberger Limited), was used for the calculation. In the Calculation Example 1, it was assumed that the first membrane separation device included a pervaporation membrane having the same structure as that of the pervaporation membrane of Measurement Example 1 and the pervaporation membrane had a membrane area of 1350 m². The concentration of IPA in a mixture (IPA+waster) to be purified was set to 5.0 wt %. The temperature of the mixture to be supplied to the first membrane separation device was set at 40° C., and the flow rate thereof was set at 290 kg/h. It was assumed that the pressure in the space in the second chamber of the first membrane separation device was decreased in such a manner that the pressure in the space was lower than an atmospheric pressure in a measurement environment by 100 kPa. It was assumed that an RO membrane was used as the filtration membrane in a second membrane separation device. It was assumed that the first concentrated fluid filling the third chamber of the second membrane separation device was pressurized to a pressure of 22.4 bar.

In Calculation Example 1, according to the calculation, the flow rate of the first permeated fluid discharged from the first membrane separation device was 73 kg/hr, and the concentration of the IPA therein was 18.4 wt %. According to the calculation, the flow rate of the first concentrated fluid discharged from the first membrane separation device was 217 kg/hr, and the concentration of the IPA therein was 0.5 wt %. According to the calculation, the flow rate of the second permeated fluid discharged from the second membrane separation device was 168 kg/hr, and the concentration of the IPA therein was 0.02 wt %. According to the calculation, the flow rate of a second concentrated fluid (waste solution) discharged from the second membrane separation device was 49 kg/hr, and the concentration of the IPA therein was 2.05 wt %. The IPA recovery rate calculated from the weight of the IPA recovered by the first permeated fluid and the second permeated fluid was 93%. The energy needed to operate the first membrane separation device was 85 kW/h, and the energy needed to operate the second membrane separation device was 1 kW/h. Table 4 shows the results.

Calculation Example 2

A material balance was calculated for a purification system as shown in FIG. 1 in the same manner as in Calculation Example 1, except that it was assumed that the first concentrated fluid filling the third chamber of the second membrane separation device was pressurized to 50 bar. In Calculation Example 2, according to the calculation, the flow rate of the second permeated fluid discharged from the second membrane separation device was 197 kg/hr, and the concentration of the IPA therein was 0.05 wt %. According to the calculation, the flow rate of the second concentrated fluid (waste solution) discharged from the second membrane separation device was 20 kg/hr, and the concentration of the IPA therein was 5 wt %. The IPA recovery rate calculated from the weight of the IPA recovered by the first permeated fluid and the second permeated fluid was 93%. The energy needed to operate the second membrane separation device was 3 kW/h. Table 4 shows the results.

Calculation Example 3

In Calculation Example 3, it was assumed that after the mixture was processed using the second membrane separation device of Calculation Example 1, a concentrated fluid discharged from the second membrane separation device was processed using the first membrane separation device of Calculation Example 1. That is, in Calculation Example 3, the order of the first separation step and the second separation step of Calculation Example 1 was changed. However, in Calculation Example 3, it was assumed that the mixture filling the third chamber of the second membrane separation device was pressurized to 93 bar. Moreover, the membrane area of the pervaporation membrane of the first membrane separation device was set to 848 m². The temperature of the concentrated fluid to be supplied to the first membrane separation device was set at 40° C.

In Calculation Example 3, according to the calculation, the flow rate of a permeated fluid discharged from the second membrane separation device was 145 kg/hr. According to the calculation, the flow rate of a concentrated fluid discharged from the second membrane separation device was 145 kg/hr, and the concentration of the IPA therein was 10 wt %. According to the calculation, the flow rate of a permeated fluid discharged from the first membrane separation device was 50 kg/hr, and the concentration of the IPA therein was 28 wt %. According to the calculation, the flow rate of a concentrated fluid (waste solution) discharged from the first membrane separation device was 95 kg/hr, and the concentration of the IPA therein was 0.5 wt %. The IPA recovery rate calculated from the weight of the IPA recovered by a permeated fluid discharged from the first membrane separation device was 96%. The energy needed to operate the second membrane separation device was 7 kW/h. The energy needed to operate the first membrane separation device was 50 kW/h. Table 4 shows the results.

TABLE 4

|  | Calculation Example 1 | Calculation Example 2 | Calculation Example 3 |
|---|---|---|---|
| Membrane area of pervaporation membrane (m$^2$) | 1350 | 1350 | 848 |
| IPA recovery rate (%) | 93 | 93 | 96 |
| Flow rate of waste solution (kg/hr) | 49 | 20 | 95 (*240) |
| IPA concentration in waste solution (wt %) | 2.05 | 5 | 0.5 |
| Energy consumed (kW/h) | 86 (PV: 85; RO: 1) | 88 (PV: 85; RO: 3) | 57 (PV: 50; RO: 7) |

*A flow rate determined when the permeated fluid discharged from the second membrane separation device is treated as a waste solution As can be understood from the results for Calculation Examples 1 and 2, a mixture containing a plurality of solvents can be efficiently purified without a lot of amount of energy by the purification method in which the purification system of the present embodiment is used. On the other hand, compared to Calculation Examples 1 and 2, the flow rate of the waste solution was large and the efficiency was low in Calculation Example 3 in which the order of the first separation step and the second separation step was changed.

Calculation Example 4

Next, a material balance was calculated for a purification system as shown in FIG. 7. A process simulator, Symmetry (manufactured by Schlumberger Limited), was used for the calculation. In Calculation Example 4, the first membrane separation device included a pervaporation membrane having the same structure as that of the pervaporation membrane of Measurement Example 1 and the pervaporation membrane had a membrane area of 1350 m$^2$. In Calculation Example 4, it was assumed that the portion of the first permeated fluid discharged from the first membrane separation device was supplied to the mixture supply passage via the first recycle passage so that the above-described recycling rate B would be 10%. Specifically, it was assumed that an aqueous solution containing 5 wt % of IPA was used as the mixture to be purified and a mixture fluid of the aqueous solution and the portion of the first permeated fluid was supplied to the first membrane separation device. The temperature of this fluid mixture was set at 40° C., and the flow rate thereof was set at 290 kg/h. It was assumed that the pressure in the space in the second chamber of the first membrane separation device was decreased in such a manner that the pressure in the space was lower than an atmospheric pressure in a measurement environment by 100 kPa. In a steady state, the concentration of the IPA in the fluid mixture to be supplied to the first membrane separation device was 5.4 wt %. It was assumed that an RO membrane was used as the filtration membrane in a second membrane separation device. It was assumed that the first concentrated fluid filling the third chamber of the second membrane separation device was pressurized to 20.8 bar.

In Calculation Example 4, according to the calculation, in a steady state, the flow rate of the first permeated fluid discharged from the first membrane separation device was 74 kg/hr, and the concentration of the IPA therein was 19.5 wt %. According to the calculation, the flow rate of the first concentrated fluid discharged from the first membrane separation device was 216 kg/hr, and the concentration of the IPA therein was 0.54 wt %. According to the calculation, the flow rate of the second permeated fluid discharged from the second membrane separation device was 166 kg/hr, and the concentration of the IPA therein was 0.03 wt %. According to the calculation, the flow rate of the second concentrated fluid (waste solution) discharged from the second membrane separation device was 50 kg/hr, and the concentration of the IPA therein was 2.16 wt %. The IPA recovery rate calculated from the weight of the IPA recovered by the first permeated fluid and the second permeated fluid was 92%. The energy needed to operate the first membrane separation device was 96 kW/h, and the energy needed to operate the second membrane separation device was 1 kW/h. Table 5 shows the results.

Calculation Examples 5 to 8

Material balances were calculated (Calculation Examples 5 to 8) in the same manner as in Calculation Example 4, except that it was assumed that the portion of the first permeated fluid discharged from the first membrane separation device was delivered to the mixture supply passage via the first recycle passage so that the recycling rate B would be the value as shown in Table 5. Table 5 shows the results.

TABLE 5

|  | Calculation Example 1 | Calculation Example 4 | Calculation Example 5 | Calculation Example 6 | Calculation Example 7 | Calculation Example 8 |
|---|---|---|---|---|---|---|
| Recycle rate B [%] | — | 10 | 20 | 30 | 40 | 50 |
| Membrane area of PV membrane [m$^2$] | 1350 | 1350 | 1350 | 1350 | 1350 | 1350 |
| Flow rate of fluid mixture [kg/h] | 290 | 290 | 290 | 290 | 290 | 290 |

TABLE 5-continued

|  | Calculation Example 1 | Calculation Example 4 | Calculation Example 5 | Calculation Example 6 | Calculation Example 7 | Calculation Example 8 |
|---|---|---|---|---|---|---|
| IPA concentration in fluid mixture [wt %] | 5.0 | 5.4 | 5.8 | 6.4 | 7.1 | 8.0 |
| IPA recovery rate [%] | 93 | 92 | 91 | 90 | 88 | 86 |
| IPA concentration in first permeated fluid [wt %] | 18.3 | 19.5 | 21 | 22.7 | 24.8 | 27.4 |
| Flow rate of first concentrated fluid [kg/hr] | 217 | 216 | 216 | 215 | 213 | 212 |
| IPA concentration in first concentrated fluid [wt %] | 0.50 | 0.54 | 0.58 | 0.65 | 0.73 | 0.84 |
| Operation pressure in second membrane separation device (RO) [bar] | 22.4 | 20.8 | 21.8 | 24.1 | 26.6 | 30.1 |
| Flow rate of waste solution [kg/hr] | 49 | 50 | 50 | 50 | 50 | 50 |
| IPA concentration in waste solution [wt %] | 2.05 | 2.16 | 2.28 | 2.58 | 2.90 | 3.33 |
| Energy consumed [kW/h] | 86 (PV: 85; RO: 1) | 97 (PV: 96; RO: 1) | 97 (PV: 96; RO: 1) | 97 (PV: 96; RO: 1) | 97 (PV: 96; RO: 1) | 97 (PV: 96; RO: 1) |

As can be understood from Table 5, by increasing the recycling rate B, the concentration of the IPA in the first permeated fluid in a steady state can be increased easily without greatly increasing the energy needed to operate the purification system.

INDUSTRIAL APPLICABILITY

The purification system of the present embodiment is suitable for purifying a mixture containing a plurality of solvents, particularly a washing solution having been used to wash a washing target.

The invention claimed is:

1. A purification system for purifying a mixture containing a first solvent, a second solvent, and an impurity other than the first solvent and the second solvent, the purification system comprising:
a first membrane separation device including a pervaporation membrane that is configured to separate the mixture into a first permeated fluid and a first concentrated fluid, the first permeated fluid having a lower concentration of the impurity than that in the mixture and having a higher concentration of the first solvent than that in the mixture, the first concentrated fluid having a higher concentration of the impurity than that in the mixture and having a lower concentration of the first solvent than that in the mixture;
a second membrane separation device including a filtration membrane that is configured to separate the first concentrated fluid into a second permeated fluid and a second concentrated fluid, the second permeated fluid having a lower concentration of the impurity than that in the first concentrated fluid, the second concentrated fluid having a higher concentration of the impurity than that in the first concentrated fluid; and
a third discharge passage connected to the second membrane separation device and configured to discharge the second concentrated fluid from the second membrane separation device,
wherein
a discharge outlet for discharging the second concentrated fluid from the third discharge passage to an outside of the purification system is arranged in the third discharge passage, and
(i) the discharge outlet arranged in the third discharge passage is configured to discharge an entire amount of the second concentrated fluid from the third discharge passage to the outside of the purification system, or
(ii) the purification system further comprises:
a concentrated fluid supply passage connected to both the first membrane separation device and the second membrane separation device and configured to supply the first concentrated fluid to the second membrane separation device from the first membrane separation device; and
a recycle passage connected to both the third discharge passage and the concentrated fluid supply passage and configured to deliver an entire amount of the remaining second concentrated fluid, which is not discharged via the discharge outlet, from the third discharge passage to the concentrated fluid supply passage.

2. The purification system according to claim 1, wherein the first solvent is a lower alcohol and the second solvent is water.

3. The purification system according to claim 1, wherein the mixture is a washing solution having been used to wash a washing target and the impurity is derived from the washing target.

4. The purification system according to claim 1, wherein the impurity is composed of an organic compound.

5. The purification system according to claim 4, wherein the organic compound includes at least one atom selected from the group consisting of a nitrogen atom and a sulfur atom.

6. The purification system according to claim 4, wherein the organic compound has a boiling point higher than a boiling point of the first solvent.

7. The purification system according to claim 1, wherein the pervaporation membrane includes a silicone resin.

8. The purification system according to claim 1, wherein the pervaporation membrane includes a matrix including a silicone resin and fillers including a zeolite and dispersed in the matrix.

9. The purification system according to claim 1, wherein the filtration membrane is a reverse osmosis membrane or a nanofiltration membrane.

10. The purification system according to claim 1, wherein the concentration of the first solvent in the mixture is 50 wt % or less.

11. The purification system according to claim 1, further comprising:
a first discharge passage connected to the first membrane separation device and configured to discharge the first permeated fluid from the first membrane separation device, and
a second discharge passage connected to the second membrane separation device and configured to discharge the second permeated fluid from the second membrane separation device, wherein
the second discharge passage joins the first discharge passage at a joining point.

12. The purification system according to claim 11, further comprising a raw material supply passage connected to the first discharge passage or the second discharge passage and configured to supply a raw material including at least one selected from the group consisting of the first solvent and the second solvent to the first discharge passage connected to the raw material supply passage or the second discharge passage connected to the raw material supply passage.

13. The purification system according to claim 1, further comprising:
a mixture supply passage connected to the first membrane separation device and configured to supply the mixture to the first membrane separation device;
a first discharge passage connected to the first membrane separation device and configured to discharge the first permeated fluid from the first membrane separation device; and
a recycle passage connected to both the mixture supply passage and the first discharge passage and configured to deliver a portion of the first permeated fluid from the first discharge passage to the mixture supply passage.

14. A method for purifying a mixture containing a first solvent, a second solvent, and an impurity other than the first solvent and the second, solvent by using the purification system according to claim 1, the purification method comprising a first separation step of decreasing, in a state where the mixture is in contact with one surface of the pervaporation membrane, a pressure in a space adjacent to the other surface of the pervaporation membrane to obtain the first permeated fluid on the other surface side and the first concentrated fluid on the one surface side, the first permeated fluid being to be reused, having a lower concentration of the impurity than that in the mixture, and having a higher concentration of the first solvent than that in the mixture, the first concentrated fluid having a higher concentration of the impurity than that in the mixture and having a lower concentration of the first solvent than that in the mixture.

15. The purification method according to claim 14, wherein the mixture is a washing solution having been used to wash a washing target and the impurity is derived from the washing target.

16. The purification method according to claim 15, wherein the first separation step is a separation step initially performed for the washing solution having been used to wash the washing target.

17. The purification method according to claim 14, further comprising a second separation step of filtering the first concentrated fluid using the filtration membrane to obtain the second permeated fluid and the second concentrated fluid, the second permeated fluid having a lower concentration of the impurity than that in the first concentrated fluid, the second concentrated fluid having a higher concentration of the impurity than that in the first concentrated fluid.

18. The purification method according to claim 17, further comprising a mixing step of mixing the first permeated fluid and the second permeated fluid.

19. A solvent manufacturing method comprising the purification method according to claim 14.

20. A purification system for purifying a mixture containing a first solvent, a second solvent, and an impurity other than the first solvent and the second solvent, the purification system comprising:
a first membrane separation device including a pervaporation membrane that is configured to separate the mixture into a first permeated fluid and a first concentrated fluid, the first permeated fluid having a lower concentration of the impurity than that in the mixture and having a higher concentration of the first solvent than that in the mixture, the first concentrated fluid having a higher concentration of the impurity than that in the mixture and having a lower concentration of the first solvent than that in the mixture;
a second membrane separation device including a filtration membrane that is configured to separate the first concentrated fluid into a second permeated fluid and a second concentrated fluid, the second permeated fluid having a lower concentration of the impurity than that in the first concentrated fluid, the second concentrated fluid having a higher concentration of the impurity than that in the first concentrated fluid, a mixture supply passage connected to the first membrane separation device and configured to supply the mixture to the first membrane separation device;
a concentrated fluid supply passage connected to both the first membrane separation device and the second membrane separation device and configured to supply the first concentrated fluid to the second membrane separation device from the first membrane separation device;
a first discharge passage connected to the first membrane separation device and configured to discharge the first permeated fluid from the first membrane separation device;
a second discharge passage connected to the second membrane separation device and configured to discharge the second permeated fluid from the second membrane separation device;
a third discharge passage connected to the second membrane separation device and configured to discharge the second concentrated fluid from the second membrane separation device;
a first recycle passage connected to both the mixture supply passage and the first discharge passage and configured to deliver a portion of the first permeated fluid from the first discharge passage to the mixture supply passage; and
a second recycle passage connected to both the third discharge passage and the concentrated fluid supply passage and configured to deliver a portion of the second concentrated fluid from the third discharge passage to the concentrated fluid supply passage.

\* \* \* \* \*